(12) United States Patent
Swyer

(10) Patent No.: US 11,534,363 B2
(45) Date of Patent: *Dec. 27, 2022

(54) MODIFYING HUMIDITY AND CONVECTION TO GLABROUS TISSUE TO CONTROL METABOLISM

(71) Applicant: Core Thermal, Inc., Everett, WA (US)

(72) Inventor: Mark L. Swyer, Mill Creek, WA (US)

(73) Assignee: Core Thermal, Inc., Everett, WA (US)

( * ) Notice: Subject to any disclaimer, the term of this patent is extended or adjusted under 35 U.S.C. 154(b) by 188 days.

This patent is subject to a terminal disclaimer.

(21) Appl. No.: 17/162,109

(22) Filed: Jan. 29, 2021

(65) Prior Publication Data

US 2021/0220215 A1 Jul. 22, 2021

Related U.S. Application Data

(63) Continuation of application No. 15/677,882, filed on Aug. 15, 2017, now Pat. No. 10,925,800, which is a
(Continued)

(51) Int. Cl.
*A61H 9/00* (2006.01)
*A61F 7/00* (2006.01)
(Continued)

(52) U.S. Cl.
CPC ......... *A61H 9/0057* (2013.01); *A61F 7/0053* (2013.01); *A61F 7/0085* (2013.01);
(Continued)

(58) Field of Classification Search
CPC ...... A61F 2007/0036; A61F 2007/0045; A61F 2007/0057; A61F 2007/0076;
(Continued)

(56) References Cited

U.S. PATENT DOCUMENTS 4,182,329 A 1/1980 Smit et al.
5,245,998 A 9/1993 Sundsrud et al.
(Continued)

FOREIGN PATENT DOCUMENTS

SU 1777864 A1 11/1992
WO WO 2006/014338 2/2006
(Continued)

OTHER PUBLICATIONS

Albrecht, Phillip et al. "A peripheral Neurovascular Pathology Associated with Fibromyalgia Patients (S17.006)", The Official Journal of the American Academy of Neurology, Feb. 12, 2013 in 2 pages.
(Continued)

*Primary Examiner* — Jonathan T Kuo
(74) *Attorney, Agent, or Firm* — Michael B. Dodd; Bold IP, PLLC

(57) ABSTRACT

Systems and methods for affecting metabolism, such as the treatment of metabolic syndrome are disclosed. A method for treating metabolic syndrome can include one or more of the steps including identifying a region of the patient comprising glabrous tissue; positioning the region of the patient comprising glabrous tissue into an enclosed chamber; adjusting the relative humidity of the enclosed chamber sufficient to create a physiologic metabolic effect; and activating a convection fan within the chamber to promote heat transfer from the glabrous tissue. The method need not involve altering the temperature within the enclosed chamber.

20 Claims, 11 Drawing Sheets

Related U.S. Application Data continuation of application No. 14/298,732, filed on Jun. 6, 2014, now Pat. No. 9,737,456.

(60) Provisional application No. 61/832,719, filed on Jun. 7, 2013.

(51) Int. Cl.
*A61F 7/02* (2006.01)
*A61H 33/06* (2006.01)
*A61H 35/00* (2006.01)

(52) U.S. Cl.
CPC .............. *A61F 7/02* (2013.01); *A61H 33/06* (2013.01); *A61H 35/00* (2013.01); *A61H 35/006* (2013.01); *A61F 2007/0036* (2013.01); *A61F 2007/0045* (2013.01); *A61F 2007/0057* (2013.01); *A61F 2007/0076* (2013.01); *A61F 2007/0239* (2013.01); *A61F 2007/0258* (2013.01); *A61H 2201/025* (2013.01); *A61H 2201/0207* (2013.01); *A61H 2201/0214* (2013.01); *A61H 2201/5084* (2013.01); *A61H 2205/065* (2013.01); *A61H 2230/045* (2013.01); *A61H 2230/105* (2013.01); *A61H 2230/305* (2013.01); *A61H 2230/505* (2013.01); *A61H 2230/605* (2013.01)

(58) Field of Classification Search
CPC ...... A61F 2007/0239; A61F 2007/0258; A61F 7/0053; A61F 7/0085; A61F 7/02; A61H 2201/0207; A61H 2201/0214; A61H 2201/025; A61H 2201/5084; A61H 2205/065; A61H 2230/045; A61H 2230/105; A61H 2230/305; A61H 2230/505; A61H 2230/605; A61H 33/06; A61H 35/00; A61H 35/006; A61H 9/0057
See application file for complete search history.

(56) References Cited

U.S. PATENT DOCUMENTS

| | | | |
|---|---|---|---|
| 6,032,877 | A | 3/2000 | Kagan |
| 7,815,581 | B1 | 10/2010 | Sung |
| 9,681,980 | B2 | 6/2017 | Swyer et al. |
| 9,737,456 | B2 | 8/2017 | Swyer |
| 10,206,811 | B2 | 2/2019 | Swyer et al. |
| 10,925,800 | B2 | 2/2021 | Swyer |
| 2004/0039432 | A1 | 2/2004 | Warriner |
| 2004/0064170 | A1 | 4/2004 | Radons et al. |
| 2004/0260524 | A1 | 12/2004 | Kim et al. |
| 2005/0114981 | A1 | 6/2005 | Shim et al. |
| 2006/0064147 | A1 | 3/2006 | Almqvist |
| 2006/0241549 | A1 | 10/2006 | Sunnen |
| 2008/0132976 | A1 | 6/2008 | Kane et al. |
| 2009/0019634 | A1 | 1/2009 | Lipponen |
| 2009/0312676 | A1 | 12/2009 | Rousso et al. |
| 2010/0022941 | A1 | 1/2010 | Pelkus |
| 2010/0305497 | A1 | 12/2010 | Tanaka et al. |
| 2011/0000484 | A1 | 1/2011 | Melsheimer |
| 2011/0066217 | A1 | 3/2011 | Diller et al. |
| 2011/0098615 | A1 | 4/2011 | Whalen et al. |
| 2011/0190856 | A1 | 8/2011 | Burke et al. |
| 2011/0239682 | A1 | 10/2011 | Raines et al. |
| 2012/0164056 | A1 | 6/2012 | Haddad et al. |
| 2012/0283626 | A1 | 11/2012 | Belson et al. |
| 2012/0296402 | A1 | 11/2012 | Kotter |
| 2012/0308670 | A1 | 12/2012 | Lipi |
| 2013/0067661 | A1 | 3/2013 | Schwirian et al. |
| 2014/0094737 | A1 | 4/2014 | Nakamura |
| 2020/0015998 | A1 | 1/2020 | Swyer et al. |

FOREIGN PATENT DOCUMENTS

| | | |
|---|---|---|
| WO | WO 2009/023750 | 2/2009 |
| WO | WO 2012/154787 | 11/2012 |
| WO | WO 2013/002482 | 1/2013 |
| WO | WO 2013/115756 | 8/2013 |
| WO | WO 2014/197863 | 12/2014 |
| WO | WO 2016/029105 | 2/2016 |

OTHER PUBLICATIONS

Chen, Hui, et al. "Adiponectin stimulates production of nitric oxide in vascular endothelial cells." Journal of Biological Chemistry 278.45 (2003): 45021-45026 in 7 pages.

Du, Yunhui, et al. "Adiponectin at Physiologically Relevant Concentrations Enhances the Vasorelaxative Effect of Acetylcholine via Cav-1/AdipoR-1 Signaling." PloS one 11.3 (2016): eQ152247 in 14 pages.

Effects of Dry Air on the Body Mar. 12, 2013, Information Please, Pearson Education, http://www.infoplease.com/ipa/A0001433.html in 1 page via Wayback Machine provided by examiner in U.S. Appl. No. 14/298,732.

Gerdle, Björn, et al. "Increased interstitial concentrations of pyruvate and lactate in the trapezius muscle of patients with fibromyalgia: a microdialysis study." Journal of rehabilitation medicine 42.7 (2010): 679-687 in 9 pages.

Guo, "Effects of aerobic exercise on lipid profiles and high molecular weight adiponectin in Japanese workers." Intern Med., 2011, 50(5), p. 389-395 (abstract) [online]. Retrieved from PubMed, PMID: 21372447.

Grahn, D.A. et al. "Heat Loss Through the Glabrous Skin Surfaces of Heavily Insulated, Heat-Stressed Individuals", J Biomech Eng 131(7), 071005 (Jun. 29, 2009) in 7 pages.

Jha, Mithilesh Kumar, et al. "Metabolic Connection of Inflammatory Pain: Pivotal Role of a Pyruvate Dehydrogenase Kinase-Pyruvate Dehydrogenase-Lactic Acid Axis." The Journal of Neuroscience 35.42 (2015): 14353-14369 in 17 pages.

Luo, Nanlan, et al. "Macrophage adiponectin expression improves insulin sensitivity and protects against inflammation and atherosclerosis." Diabetes 59.4 (2010): 791-799 in 9 pages.

Omae, Tsuneaki, Taiji Nagaoka, and Akitoshi Yoshida. "Relationship Between Retinal Blood Flow and Serum Adiponectin Concentrations in Patients With Type 2 Diabetes MellitusRetinal Blood Flow and Adiponectin." Investigative ophthalmology & visual science 56.6 (2015): 4143-4149.

Song, J. et al., "Association Between Risk Factors for Vascular Dementia and Adiponectin", BioMed Research International, 2014 in 14 pages.

Extended European Search Report for EP 15834125.5 dated Feb. 16, 2018 in 7 pages.

Office Action dated Oct. 11, 2016 in U.S. Appl. No. 14/298,732 in 12 pages.

Office Action dated Oct. 7, 2016 in U.S. Appl. No. 14/832,715 in 25 pages.

Search Report and Written Opinion in PCT/US2014/041409 dated Sep. 25, 2014 in 8 pages.

Search Report and Written Opinion in PCT/US2015/046277 dated Oct. 29, 2015 in 7 pages.

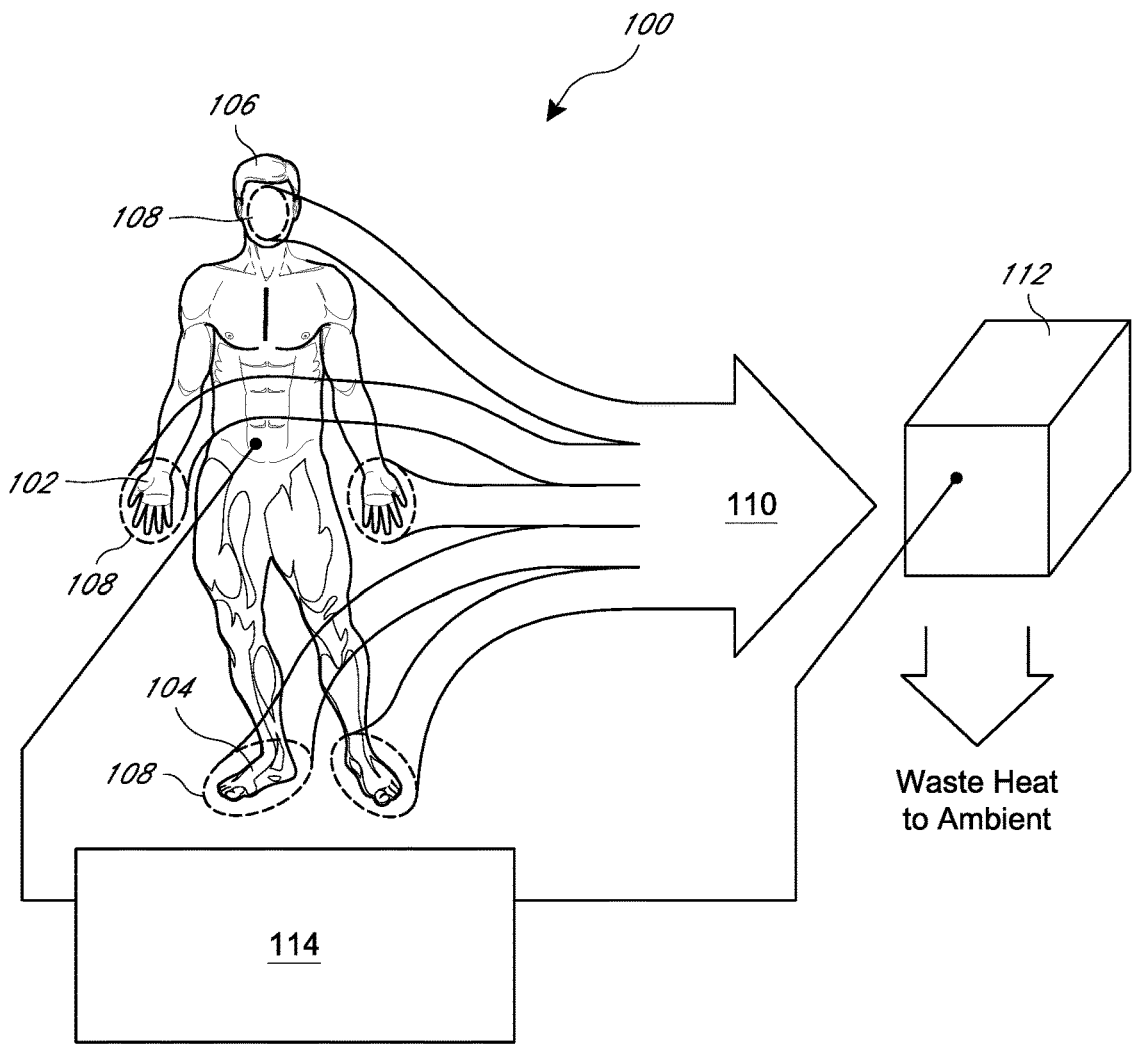
*FIG. 1*
Vacuum Options
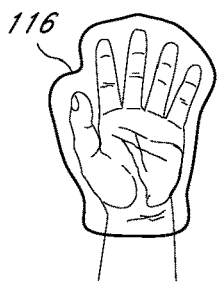
Fully Enclosed
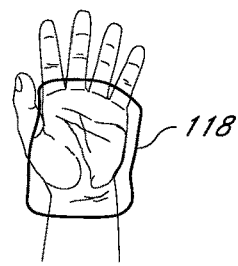
Fingers Exposed
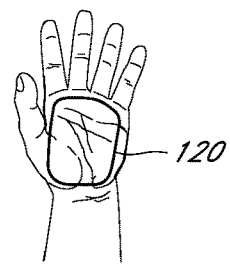
Patch
*FIG. 2*

MODIFYING HUMIDITY AND CONVECTION TO GLABROUS TISSUE TO CONTROL METABOLISM

PRIORITY CLAIM

This application claims the benefit under 35 U.S.C. § 120 as a continuation of U.S. application Ser. No. 15/677,882 filed on Aug. 15, 2017, which in turn claims the benefit under 35 U.S.C. § 120 as a continuation of U.S. application Ser. No. 14/298,732 filed on Jun. 6, 2014, which in turn claims the benefit under 35 U.S.C. § 119(e) as a nonprovisional of U.S. Prov. Pat. App. No. 61/832,719 filed on Jun. 7, 2013, each of the foregoing of which are hereby incorporated by reference in their entireties.

BACKGROUND

The application relates to systems and methods for affecting glabrous skin, including controlling humidity and/or convection, for example, and in some cases independently of temperature control.

Chronic medical conditions including metabolic syndrome, diabetes mellitus, dyslipidemia, hypertension, obesity, coronary, cerebrovascular, and peripheral vascular disease, among others, contribute to significant morbidity and mortality. First-line therapies including diet and exercise are often difficult to adhere to by patients. Taking medications also requires compliance, and medications can also have significant side effects and drug-drug interactions. Surgical procedures involving gastric restriction and/or gastric and intestinal malabsorption, for example, also can have significant risks and morbidity. What is needed is a non-invasive, comfortable, well tolerated therapy to treat and/or prevent the aforementioned medical conditions, among others.

SUMMARY

In some embodiments, disclosed are systems and methods which enable the body to promote heat loss, such as through glabrous tissue, without necessarily changing the temperature of the environment surrounding the patient or a selected portion of the patient. This can be accomplished by altering the humidity and/or promoting air circulation via convection, which together can have unexpectedly synergistic effects. Not to be limited by theory, doing so can stimulate a host of beneficial metabolic pathways, such as, for example, improving insulin resistance, increasing glucose uptake, stimulating adiponectin production, normalizing lipid metabolism, reducing vascular smooth muscle proliferation, causing vasodilation and blood pressure reduction via nitric oxide and other mechanisms, triggering lipolysis such as via PPARG, and activating brown adipose tissue.

An aspect of some embodiments of the invention relates to increasing a body metabolism of a subject by increasing loss of heat from the body without necessarily altering the temperature surrounding a selected portion of the body, such as, for example, glabrous tissue. In some embodiments of the invention, the effect is to alter adipocytokine production, such as increasing adiponectin, increase glucose uptake, decrease insulin resistance, increase lipolysis, activate brown adipose tissue, decrease smooth muscle proliferation, and relax smooth muscle, for example. In some embodiments, systems and methods can effect weight loss, for example of at least about 1, 2, 3, 4, 5, 7, 10, 15, or more pounds. In some embodiments of the invention, heat loss is increased by causing vasodilatation, optionally on an exposed body part. In some embodiments, heat loss is increased by altering the humidity and/or directing a convection air flow toward a target region of the patient.

Optionally, the rate at which the dehumidified air and/or air flow via convection removes heat from the body is actively controlled, and modified in response to a sensor sensing one or more physiologic parameters of the patient in a closed feedback loop. In some embodiments, heat is removed in a manner which avoids or reduces pain or discomfort to the patient. In some embodiments, heat is removed in a manner which prevents and/or overcomes vasoconstriction. In some embodiments, the heat is removed without lowering the core body temperature significantly, for example without lowering it by more than 1 degree Celsius, or by more than 0.5 degrees, or by more than 0.2 degrees.

In some embodiments, heat loss is sustained over a long enough time, at a high enough rate, and/or at a high enough duty cycle, so that the base metabolism of the subject increases, and remains elevated even when the patient is not being treated.

A controller 106 optionally controls rate of airflow convection as well as the humidity of the air in the region surrounding the body tissue to be treated. Controller can perform these functions this in response to input from one or more sensors, in a closed feedback loop. The sensors include, for example, one or more of a sensor which measures the intensity of shivering by the subject; a sensor which measures blood flow or pressure; and a sensor which measures temperature, for example one or more of the temperature, humidity, or other parameters. As will be described in more detail below, one or more feedback loops optionally allow the cooling system to operate in a regime where blood flow is not reduced by vasoconstriction, and/or where the system and method does not cause discomfort.

In some embodiments of the invention, there is a sensor which measures base metabolic rate, for example by measuring oxygen consumption while the subject is resting, and the system removes heat from the body at a great enough rate or average rate, over a long enough period of time, to raise the subject's basal metabolic rate over a long term, as measured by the sensor. Optionally, the subject's basal metabolism goes up by at least 5%, 10%, 15%, 20%, 25%, 30%, 35%, 40%, 45%, 50%, or more, and the increase lasts for at least one day, or at least one week, or at least one month. In some embodiments, the basal metabolic rate is measured at times when the system is not activated, in order to verify the long term nature of the increase in base metabolism induced by the system. In some embodiments, for example, the concentration of oxygen and/or the concentration of carbon dioxide is measured in a face mask worn by the subject while inhaling and exhaling. The raw data is optionally analyzed by controller to find the rate of oxygen consumption, for example by multiplying the breathing rate by the change in oxygen volume or the change in carbon dioxide volume per breath.

Using feedback and/or other methods (to be described below), to reduce or avoid vasoconstriction, has the potential advantage that it can increase metabolism more effectively than an uncontrolled temperature change. These methods may not need to be used for a very long time to be effective. Using feedback and/or other methods (to be described below) to avoid discomfort, on the other hand, has the potential advantage that a subject may tolerate the use of a system for a longer period of time than if a cooling or heating system were used. For either or both these reasons, patients may continue the use of the system for a long enough time to achieve a particular beneficial effect. This may allow the system to be used safely at home, without supervision of a physician.

In some embodiments, disclosed is a method for treating a patient, comprising one or more of the steps of identifying a region of the patient comprising glabrous tissue; positioning the region of the patient comprising glabrous tissue into an enclosed chamber; and applying a gas having a preselected first relative humidity selectively to a region of the patient comprising glabrous tissue within the enclosed chamber, wherein the first relative humidity is less than about 30%, 25%, 20%, 15%, 10%, 5%, or less. The method can also include activating a fan configured to promote heat loss from the glabrous tissue without changing the temperature of the air within the enclosed chamber. In some embodiments, the method is sufficient to increase the basal metabolic rate of a patient by at least 5%, 10%, 15%, 20%, 25%, or more in a 24 hour period following the treatment. In some embodiments, the method is sufficient to alter, such as reduce the core temperature of the patient by about, at least about, or no more than about 0.2, 0.4, 0.6, 0.8, or 1.0 degrees Celsius. In some embodiments, the method is sufficient to increase or decrease a metabolic or other parameter in the patient by at least about 5%, 10%, 15%, 20%, 25%, 30%, 35%, 40%, 45%, 50% or more measured at a specified time after the therapy (compared with a measurement prior to or at the start of therapy), such as 1 day, 2 days, 3 days, 4 days, 5 days, a week, 2 weeks, a month, 2 months, 3 months, or more. In some embodiments, the parameter could be an change e.g., increase in adiponectin, HDL cholesterol, and/ or a change, e.g., decrease in total cholesterol, LDL cholesterol, VLDL cholesterol, triglyceride, glucose, fructosamine, Hemoglobin A1c, leptin, cortisol, plaque calcification thickness or diameter, systolic, diastolic, or mean blood pressure, or another parameter.

The method can be sufficient to improve one or more of, for example, diabetes mellitus, dyslipidemia, metabolic syndrome, obesity, and hypertension. The method need not modify the temperature within the enclosed chamber. In some embodiments, the air surrounding the patient outside of the enclosed chamber has a second relative humidity, wherein the second relative humidity is at least about 30%, 35%, 40%, 45%, 50%, or more. The applying step can be done intermittently, or continuously for about or at least about 30 minutes, 60 minutes, 90 minutes, 2 hours, 3 hours, 4 hours, 5 hours, 6 hours, 8 hours, 10 hours, 12 hours, or more. The method can be repeated at a specified interval, such as 1, 2, 3, 4, 5, 6, or more times daily for at least about 1, 2, 3, 4 weeks, or more. The method can also include sensing a physiologic parameter of a patient, and adjusting the first relative humidity and/or convection air flow in response to the sensing of the physiologic parameter. The region of the patient that includes glabrous tissue to be treated can be a palmar and/or plantar surface of the patient. The enclosed chamber can take the form of a glove, a boot, or a shoe and configured to allow the patient to ambulate while the patient's region comprising glabrous tissue within the chamber. Negative pressure can also be applied to the glabrous tissue during the method.

Also disclosed herein is a method for treating metabolic syndrome, including one or more of the steps of identifying a region of the patient comprising glabrous tissue; positioning the region of the patient comprising glabrous tissue into an enclosed chamber; adjusting the relative humidity of the enclosed chamber, such that the relative humidity of the enclosed chamber is less than about 20%; and activating a convection fan within the chamber to promote heat transfer from the glabrous tissue. In some embodiments, the method does not involve altering the temperature within the enclosed chamber. The method, in some cases, can cause at least 5, 10, 15, 20, 25, 30, 35, 40, 45, 50, 75, 100, 125, 150, 175, 200, 250, 300, 400, 500 or more kilocalories of heat to be lost from the patient within a time period of about 10 minutes, 15 minutes, 30 minutes, 45 minutes, 1 hour, 2 hours, or more.

Also disclosed herein is a system for stimulating the glabrous tissue of a patient. In some embodiments, the system includes one or more, or all of the following: a rigid or semi-rigid housing surrounding a chamber; a gas compressor configured to supply de-humidified air to the chamber; an inlet fluidly connecting the gas compressor to the chamber; a patient port operably connected to the chamber and configured to house an extremity of a patient comprising the glabrous tissue, the patient port having a seal such that upon insertion of the extremity of the patient into the chamber a substantially air-tight seal in an interior of the chamber; a power source; a gas outlet fluidly connected to the chamber; a convection fan configured to flow air to the glabrous tissue sufficient to create a therapeutic effect; and a controller configured to adjust the relative humidity of the de-humidified air into the chamber. In some embodiments, the system does not comprise a heating or cooling element to alter the temperature of the interior of the chamber. The system can further comprising a source of vacuum configured to apply a negative pressure to the interior of the chamber, and include at least one humidity sensor within the chamber. The gas compressor can comprise an oxygenator. The system can be at least partially in the shape of a shoe configured to be worn by the subject to treat plantar glabrous tissue of the patient, or at least partially in the shape of a glove configured to be worn by the subject to treat palmar glabrous tissue of the patient.

BRIEF DESCRIPTION OF THE DRAWINGS

FIG. 1 illustrates an embodiment where heat is removed from the glabrous skin target areas of palms, soles, and face.

FIG. 2 illustrates three non-limiting end-effector configurations for the hand.

DETAILED DESCRIPTION

Figure 3:
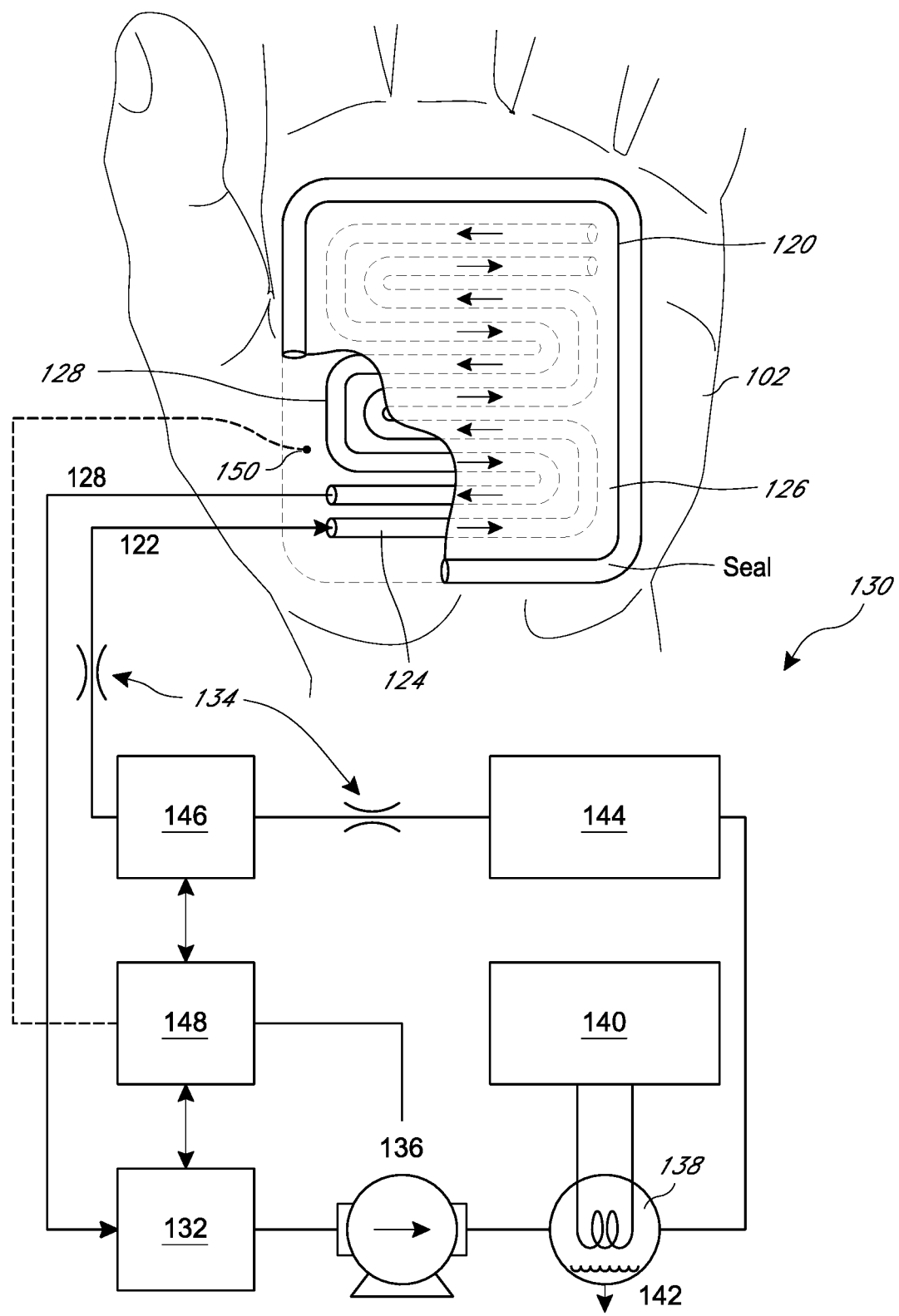
FIG. 3 shows schematically one embodiment for a forced air convection system.

In some embodiments, disclosed is a device which enables the body to promote rapid heat loss. The device can be configured to affect the glabrous tissues, including that of the palms and soles. These glabrous tissues are unique in the human body. Glabrous tissues provide body surface access directly to the hypothalamus, which is the body's thermal control center. Glabrous tissues generally have a surface without hairs or projections. In some embodiments, the heat loss can be accomplished without changing or substantially changing the temperature of the environment, e.g., the air surrounding the selected tissue of the patient to be affected.

In some embodiments, the device removes heat for the body core and directly reduces the core body temperature. The reduced core body temperature has been shown to have beneficial effects in the health of human beings. In some embodiments, the device can affect humidity and/or convection (e.g., via one or more fans) of the air surrounding the glabrous tissue without necessarily changing air temperature, which can lead to beneficial physiologic effects.

Not to be limited by theory, but these benefits can include, for example, any one or number of the following:

1) Reduction of central obesity
2) Overall weight loss by enhanced caloric loss
3) Reduction of insulin resistance, such as at the receptor level via adiponectin. The result is increased uptake of glucose and reversal of diabetes and pre-diabetes.
4) Correction of abnormal lipid metabolism through hormonal changes, involving adiponectin with reduction of triglycerides and increasing HDL
5) Reduction of smooth muscle cell proliferation in human arteries, again through adiponectin effects. This can improve blood pressure and hypertension (including via the release of nitric oxide), and improve arterial blood flow with less atherosclerotic buildup in arteries; and thus treat or prevent arterial-vascular disease including coronary artery disease, peripheral artery disease, and cerebral vascular disease.
6) Adipocytokines can trigger peroxisome proliferator-activated receptor gamma (PPARG), which in turn can trigger fat thermogenesis/lipolysis. Fat is reduced in the muscle, liver, and/or pancreas, which increases insulin sensitivity, release, and glucose uptake. The hypothalamus can then sense peripheral heat transfer, and activate adipocytokine release through the sympathetic nervous system.
7) Activation of brown adipose tissue (BAT) cells, discussed further below.

The reduced core temperature directly impacts the hypothalamus; which is the body's center for many physiologic effects. When the hypothalamus senses changes in the peripheral body tissues, it triggers hormones which will warm the core body organs. When temperature is reduced, these hormones up-regulate metabolism to increase body heat. In some embodiments, the devices can remove body heat. This feeds back to the hypothalamus, which increases body heat, which in some cases can lead to a virtuous cycle of enhanced metabolism.

There is a direct effect of a lower body core temperature on Brown Adipose Tissue (BAT). Lower temperature activates BAT cells. These cells are uniquely loaded with mitochondria. Mitochondria are the cells' energy production plants. They normally produce ATP molecules which are the body's currency for energy. Energy is normally stored as ATP and mitochondria are the only place where a cell can produce ATP.

The BAT cells are unique in turning off ATP production when body heating is required. The BAT cells contain UCP1, which is an uncoupling protein. This protein stops ATP production. These proteins uncouple the ATP process called oxidative phosphorylation and ATP production is diverted to heat production.

The BAT cells break down fatty acids in this process. This breakdown process is called lipolysis. The BAT cells, again, are unique cells breaking down fatty acids and creating heat. The generated heat is transmitted thru the blood stream to our device; at the glabrous tissue. Glabrous tissue is highly vascularized in the form of arterial-venous-anastomoses (AVAs). Thus a high amount of heat is expelled out of the body at these AVA's, through the glabrous tissue. As more heat is lost in this process, temperature is lowered which stimulates the BAT cells to produce further heat and sets up a virtuous cycle of heat loss, calorie loss leading to weight loss.

Heat loss will vary based on how many BAT cells are present in each individual. The greater the residual stores of BAT, the greater the amount of heat loss and calorie loss. BAT cells are most prominently in human infants. BAT deposits are located around sternal tissue, interscapular tissue, and paracervical tissue. The quantity of BAT recedes as one ages. Most adults have small amounts of residual BAT. These deposits recede further with obesity. Adults in thermogenesis studies have been PET-scanned and BAT deposits have clearly been identified.

Constitutive BAT (CBAT) has also been observed to stimulate white adipose tissue to become recruitable BAT (rBAT). This rBAT is called beige BAT. rBAT is found in WAT and skeletal muscle. rBAT is found as inherited congenital BAT at interscapular and peristernal areas.

Adiponectin (also referred to as GBP-28, apM1, AdipoQ, and Acrp30) is the most plentiful hormone in the human body. It is secreted by, for example, visceral WAT. This hormone is one of many hormones or adipocytokines secreted by WAT and BAT. Adipocytokines include adiponectin, leptin, resistin, visfatin, adipsin, and the like. Leptin, resistin, and tumor necrosis factor-alpha (TNF-α) production is increased in hypertrophic fat cells, which are less sensitive to insulin. Fatty tissue has been found to be a very metabolic tissue. The adiponectin levels have increased by cold exposure. Adiponectin increases insulin sensitivity. It decreases blood pressure by release of nitric oxide (NO). NO increases arterial dilatation. Adiponectin also reduces proliferation of smooth muscle cells in systemic arteries and arterioles. The reduction of smooth muscle cells in arteries reduces cholesterol adherence to arteries. This reduces atherosclerotic burden in vessels. In some embodiments, systems and methods herein can increase adiponectin levels, upregulate adiponectin receptors, and/or increase receptor sensitivity to adiponectin, among other effects.

Adiponectin also increases insulin receptor sensitivity, such as in peripheral tissues. Glucose is more readily taken up by muscle cells reducing diabetes and pre-diabetes. Patients with Type-2 diabetes, obesity, and smokers reduce levels of adiponectin. lean body mass and lower alcohol levels have higher levels of adiponectin. Glucocorticoids and adrenergic stimulators also reduce adiponectin levels.

The circulating level of adiponectin at three to 30 μg/ml can be the highest concentration of all body hormones, and sometimes about 1,000 times greater than insulin. Adiponectin typically has a half-life in the body of minutes to hours, such as about 1-3 hours, such as about 75 minutes or about 2.5 hours, and is primarily cleared by the liver. Adiponectin structurally belongs to the complement 1q family and is known to form a characteristic homomultimer. Human adiponectin is present in high (HMW), middle (MMW) and low (LMW) molecular forms that correspond to a multimer, hexamer and trimer. Adiponectin circulates in human plasma mainly as a 180-kDa middle molecular weight (MMW) hexamer and a high molecular weight (HMW) multimer of approximately 360 kDa. A proteolytic cleavage product of adiponectin, known as globular adiponectin (gAd), also circulates in human plasma. Analyses by sedimentation equilibrium centrifugation and gel electrophoresis revealed that HMW adiponectin is octadecameric.

In some embodiments, systems and methods envelope glabrous skin enabling heat extraction from the body. This can remove heat from the body at a temperature where shivering does not occur. Systems and methods can activate BAT cells in some users.

In some embodiments, systems and methods include material that envelopes one or more hands and/or feet. The cover creates a seal around the wrists and ankles, for example, to create a vacuum which will induce increased blood flow to the area. Fluid (gas or liquid), such as air, will be circulated into the area under vacuum. The fluid will be continuously cooled by a heat exchange system that is channeled through the coverings. In some embodiments, systems and methods can be automated to account for ambient temperature, user's location, and/or user's sleep cycle.

In some embodiments, the user would use a device over an extended period of time, such as, for example, about or at least about 1, 2, 3, 4, 5, 6, 7, 8, 9, 10, 11, 12, or more hours a day. In another preferred embodiment, the Apparatus would be used during sleep. In another preferred embodiment, the apparatus can be applied to the forehead, for example, to reduce fever or otherwise decrease body temperature.

FIG. 1 illustrates an embodiment where heat is removed from the glabrous skin target areas of palms 102, soles 104 and face 106. Thermal end effectors 108 (the element at the terminus of the functional circuit) contact the target zones 102, 104, 106 on the patient 100 and act to remove thermal power (heat/time) from the patient 100. The heat removal device 112 may either be worn by the user or remote from the user (e.g., under the bed) and acts to move the heat 110 from the target cooling zones 102, 104, 106 of the end effectors 108 and expel it to the room. In some embodiments, a control system 114 can optionally monitor patient characteristics to modulate thermal power 110 removal from the patient.

The modes of heat release, e.g., cooling can include:
1. Forced air convection—air flows over the skin
2. Forced liquid convection—liquid flows directly over the skin
3. Conductive—A thermally conductive material contacts the skin and wicks heat through it towards a thermal reservoir.
4. Radiative—Heat transfer via infrared radiation from the skin to a cooler target surface or surroundings.

In some embodiments, it can be beneficial to apply a vacuum of, for example, about 0.10 atm to about 0.50 atm to selected glabrous skin in order to encourage blood perfusion into the target zones.

Some embodiments can be either in an open or closed loop configuration. In the open loop embodiment, the heat removal device would not consider patient data to modulate or modify its control settings. It can still be configured to control some internal measurement variable such as the temperature of the end effectors, amount of power output or rate of energy removed. However, it may not use patient characteristics directly to modulate the output.

The closed loop system would employ the information from patient sensors to modulate the heat removal operations. Possible non-limiting characteristics for measurement include one or more of the following:
1. Temperature
   a. Forehead
   b. Axillary
   c. Inguinal
   d. Tympanic
   e. Esophageal
   f. Palmar
   g. Solar (foot)
2. Sweat sensor
   a. Resistive
   b. Chemical
3. pH sensor
4. Shiver sensor
   a. Accelerometer, multi axis accelerometer.
   b. Electromyography or electromyelography
5. EKG
6. EEG
7. Blood pressure Multiple sensors can be used. Either an open or closed loop system can be clinically advantageous. The open loop system, in some embodiments, can incorporate some user control of intensity and be a less expensive implementation. In some embodiments, the systems and methods herein can decrease systolic, diastolic, or mean arterial pressure by about or at least about 5, 10, 15, 20, 25, 30, or more mm Hg measured an hour, 2 hours, 3 hours, 4 hours, 6 hours, 12 hours, 18 hours, 24 hours, 2 days, 3 days, 1 week, 2 weeks, 1 month, or more after treatment.

The glabrous skin locations at the upper and/or lower extremities, for example, offer a variety of advantageous connection options for the end effector. For instance in FIG. 2, three non-limiting general options for the hand are illustrated. The hand or foot may be fully enclosed by a rigid or semi-rigid housing 116, the fingers or toes may be allowed to be located outside of the vacuum housing 118 (for comfort or other reasons) while the palm of the hand remains within the vacuum housing 118 or the effector may be localized over a given patch 120 of skin with a perimeter seal. In some embodiments, a soft elastomeric seal is anticipated as well as a rigid or semi-rigid outer housing to resist the vacuum forces and allow increased perfusion in the treated skin.

Ports into and out of the end effectors can help create a dry and comfortable environment with the effector. Effectors can, in some embodiments contain inner media that touches the skin and helps support the effector housing such that a soft housing does not collapse to the skin under vacuum.

FIG. 3 shows schematically one embodiment for a forced air convection system. Here the end effector may take the form of, for example, any of the embodiments shown in FIG. 2, although the patch 120 over the palmar glabrous tissue 102 is shown here. Starting from the inlet 122 to the end effector 120, air, such as cool air is introduced into a dead-end tube that may include small perforations (holes) 124 along its length. The cool air is allowed to exit these holes 124 and enter the chamber 128 between the rigid or semi-rigid housing 126 (covering) and the skin 102. The chamber could incorporate one or more sensors 150 as described elsewhere herein. In some embodiments the perforations 124 would be sized and located such that the cool air was encouraged to accelerate and flow over the skin 102. As it passes in close proximity to the skin 102, the air picks up heat through a process of convection. The air is subsequently drawn into similar perforations on a similar dead-end tube that acts as the outlet 128. The warm air now travels down the outlet tube 128. Either or both of the inlet 122 and outlet 128 tubes can incorporate insulation between the end effector 120 and the heat removal device to minimize parasitic heat transfer with respect to the environment. As the air enters the heat removal device 130 it encounters one or more sensors 132 for temperature, pressure, flow, and/or humidity. In some embodiments, a mass flow sensor based on thermal transfer can be used, such as those from Honeywell (Morristown, N.J.), e.g., the Honeywell AWM43300V microbridge mass airflow sensor).

Some types of sensors 132 can report mass flow directly without requiring knowledge of pressure. In some embodiments, the mass flow sensor 132 would report both the flow and the air temperature. Some examples of mass flow sensors that can be used or modified for use with embodiments herein include those from TSI Inc. (Shoreview, Minn.). In another embodiment the flow sensor 132 would be based on a pressure differential across a known constriction 134 or resistance to air flow. In some embodiments, the air flow would be estimated from the differences in pressure between the outlet and inlet. In another embodiment the flow would be estimated from the speed of the pump driving the airflow. In another embodiment, the flow would be estimated by a paddle wheel sensor.

In some embodiments, the cross-sectional area of the flow path can be varied to make best use of the sensors 132. For instance, the air flow into the system can first pass through the flow sensor 132 with a cross-sectional flow area equal to or smaller than the return tube itself. This can be preferred in some cases because it maintains a high particle velocity and thus gives a larger signal to the flow sensor 132. Once exiting the flow sensor 132 the air would enter a flow region of a much larger cross section thus slowing the particle velocity for relative humidity measurements which typically have much slower time constants. The location of the temperature and pressure sensor could also be selectively positioned to make best use of their range and response time.

Upon exiting the inlet sensor array 132, the air would enter the inlet side of the pump 136. This point of the system would be the lowest pressure within the entire system and serves to generate the vacuum required to maintain negative pressures within the end effector housing. The pump 136 itself may be of the rotary vane, wobble pump, piston, gear pump, diaphragm pump, peristaltic pump, centrifugal fan, axial fan variety or other mechanical pumping means. The pump 136 adds work to the air, increasing its pressure such that the pressure at the outlet is the highest pressure within the system and acts to drive the flow of air through the patient circuit.

The air now enters a heat exchanger 138. The heat exchanger 138 may accommodate heat transfer from the air to another working fluid such as air or water. This working fluid would then be cooled by other means such as evaporative cooling, connection with a refrigeration cycle 140 (vapor-compression, Stirling, etc.) or thermo-electric cooling (Peltier, etc.). The heat exchanger 138 may accommodate transfer of heat convectively from the air and conduct it directly into the expansion chamber of a vapor-compression refrigeration cycle 140, the heat absorption zone of a Stirling engine, the cold side of a thermo-electric cooler, a chemical cooling bath, an ice bath and/or, simply to ambient room air convectively (external fan).

In some embodiments, this cooling process is performed downstream from the pump 136 such that it acts as an intentional pressure drop thus lowering the pressure at the end effector 120 without the need for additional flow restriction.

If the relative humidity of the air exceeds the dew point during this cooling process then moisture will condense out, preferentially lowering the moisture content of the outbound air. Accommodations for removal of this condensate 142 will be incorporated here in the form of a reservoir, drain or adsorbent bed.

It may be desirable to further lower the humidity of the outbound air. In this case an additional dryer stage 144 can be incorporated downstream of the chiller stage 138. This stage 144 may include a desiccant bed using adsorbent materials such as silica gel, activated charcoal, calcium chloride or zeolite, for example. In one embodiment the desiccant can be periodically changed by the user. In another embodiment the desiccant can be recharged by heating the bed after the treatment cycle. In another embodiment the dryer 144 can incorporate multiple beds and valves to implement a pressure swing adsorption drying process.

After the cooler 138 and drying 144 stages the pressure may not be low enough to ensure the appropriate negative pressures within the end effectors 120. An intentional restriction 134 may need to be placed in the flow path to lower the pressure of the outlet air. In some embodiments, this is done prior to the outlet sensor array 146 to minimize the pressure difference between the outlet and inlet sensor arrays. It may be possible to eliminate either the outlet 146 or inlet 132 pressure sensors in this case.

The outlet sensor array 146 can be identical to the inlet sensor array 132 with the preferential order reversed in some cases. The air first reaches the humidity sensor within a larger cross-sectional area then reaches the flow and temperature sensors in the smaller cross-sectional flow area.

Immediately prior to entering the end effector 120, an additional user-controlled restriction may be incorporated to allow convenient control of the vacuum level. Additionally, a shut-off valve or valve that opens to ambient can be incorporated here to allow the user to turn the vacuum off for easy removal of the end effector 120.

A programmable controller device 148 such as a microcontroller circuit is configured to monitor the signals from the inlet 132 and outlet 146 sensor arrays and optionally any patient characteristic sensors. The controller 148 also may monitor and control the function of the pump 136, chiller 138, dryer 144, and restriction 134 (if it is an active valve such as a proportional valve). This allows the controller 148 to monitor the status of the system and modulate settings to maintain a desired target such as heat lift from the patient.

In one embodiment, the sensors and controller do not exist and the system is purely an open loop device. Here the patient or operator may adjust some flow controls such as knobs to achieve the desired operating conditions.

In another embodiment the controller 148 uses the sensor information to calculate the enthalpy of the incoming air (high) and the outgoing air (how). The difference in enthalpy values gives an estimate for the heat removed from patient.

Some details of how this is done can be found at http://www.engineeringtoolbox.com/enthapy-moist-air-d_683.html.

In some embodiments, the factors here including the combination of flow, temperature, pressure and humidity sensing at both inlet and outlet allow for an accurate calculation. The latent heat of vaporization from evaporation of perspiration can be a significant cooling factor. Some embodiments may optionally incorporate an additional cooling mist or spray onto the skin which is then evaporated by the dry inlet air to the end effector.

Figure 4:
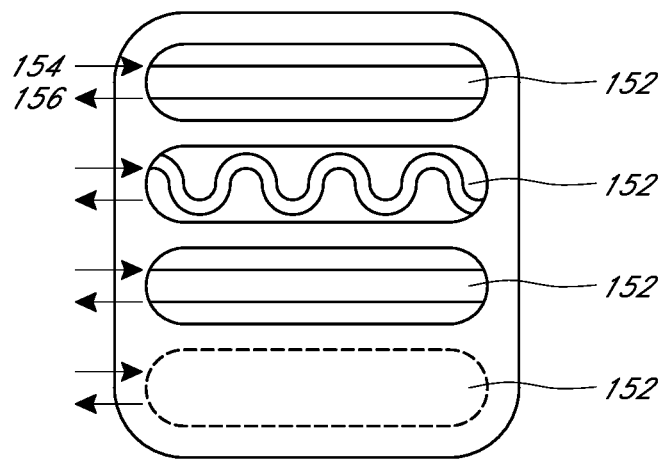
FIG. 4 illustrates an embodiment in which there can be a plurality of vacuum chambers separated by a soft or rigid seal within an end effector.

FIG. 4 illustrates an embodiment in which there can be a plurality of vacuum chambers 152 separated by a soft or rigid seal within an end effector. These chambers 152 may be plumbed with their own inlet 154 and outlet 156 lines, which may be perforated tubes as previously described. Alternatively, they may share a common inlet line or a common outlet line. In any of these cases, the separate chambers 152, in cooperation with electronically, pneumatically or mechanically actuated valves within the heat removal device, allow the vacuum pressure within each chamber 152 to be altered somewhat independently from the others. This pressure cycling results in a corresponding cycling of the local vaso-dilation resulting in a flushing effect and improved refreshing of the blood flow within the AVA.

Figure 5:
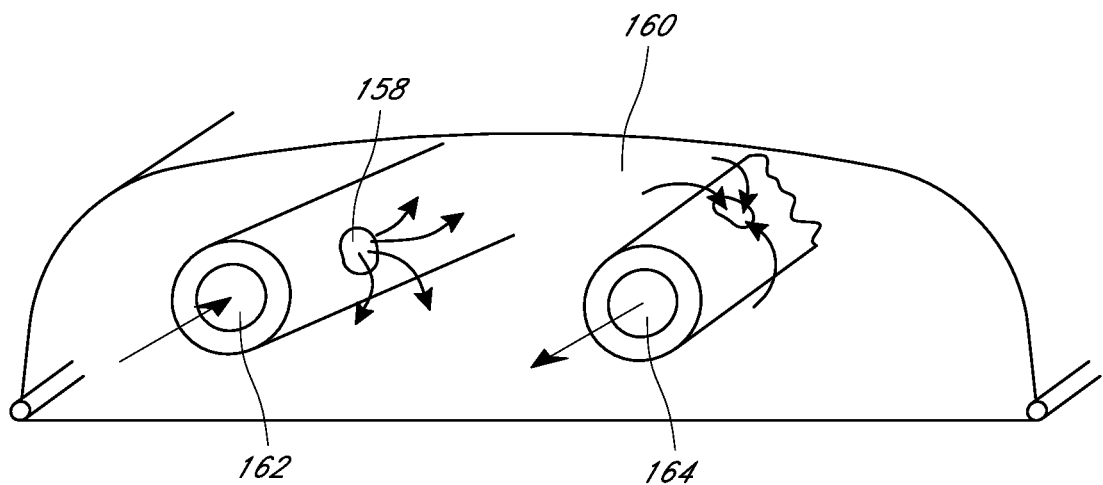
FIG. 5 illustrates an embodiment of perforated tubes within a given chamber.

FIG. 5 illustrates an embodiment of perforated tubes within a given chamber. The cool air enters the inlet 162, exits small holes 158, enters the chamber 160 and picks up heat from the skin, then is drawn into the outlet 164 tube by the negative pressure. Heat transfer may in some cases preferentially be enhanced by a non-cylindrical cross-section, measures to keep the tubes close to the skin, and number and size of the tubes themselves.

Figure 6:
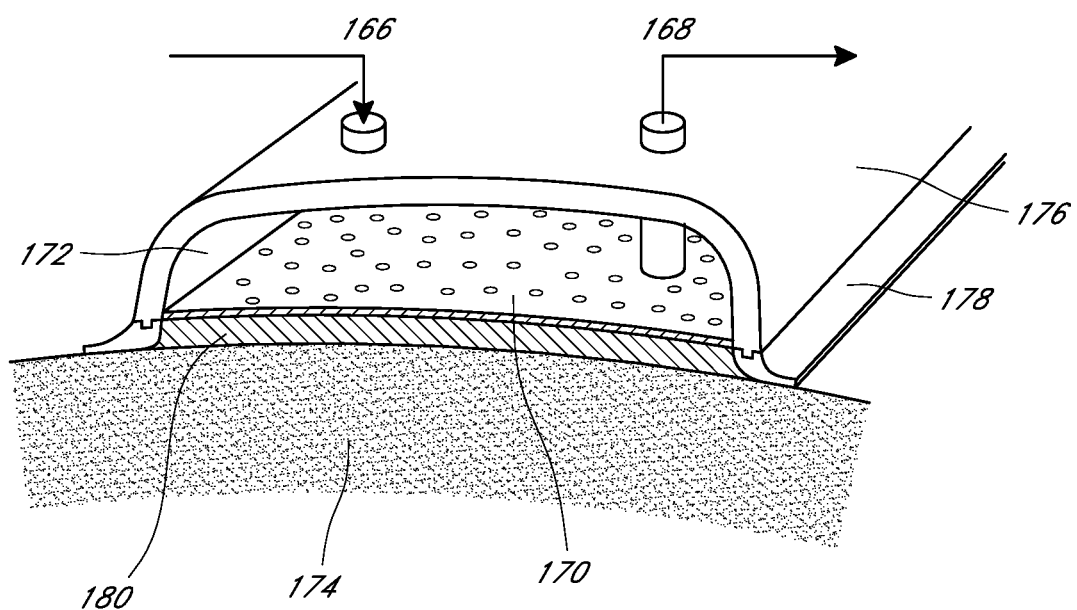
FIG. 6 illustrates another embodiment for forced convection.

FIG. 6 illustrates another embodiment for forced convection. The cool air enters the chamber 172 via an inlet 166 opposite the skin 174. It is separated by a porous barrier 170 separating the portion of the chamber 172 close to the skin 174 from the portion opposite. The wall of the chamber 172 is formed by a housing 176 which can be rigid in some cases. A seal 178 can be created with the skin surface 174.

One or more air outlets 168 draw air away from the side of the chamber 172 closest to the skin 174. The cool air picks up heat from the patient and carries it away from the chamber 172.

In some embodiments, the porous barrier 170 could be a metal mesh. In another embodiment the pores are restrictive enough that the velocity of the air is increased dramatically upon exiting the pores (nozzle effect). In another embodiment the porous barrier 170 is very close to the skin such that the high velocity air impinges on the skin surface 174. Additionally the barrier 170 can form a larger inlet chamber volume to allow the cool air to evenly distribute throughout the upper chamber. In another embodiment the porous barrier 170 is formed by a layer of open cell foam 180 in contact with the skin. In a related embodiment, the barrier 170 is a semi-permeable mesh or cloth glove or sock within a rigid or semi-rigid outer glove or boot. In another embodiment the barrier 170 incorporates pores in a nonuniform (gradient) pattern to compensate for pressure differentials throughout the flow path. This gradient pattern leads to a more uniform cooling pattern in some cases.

Figure 7:
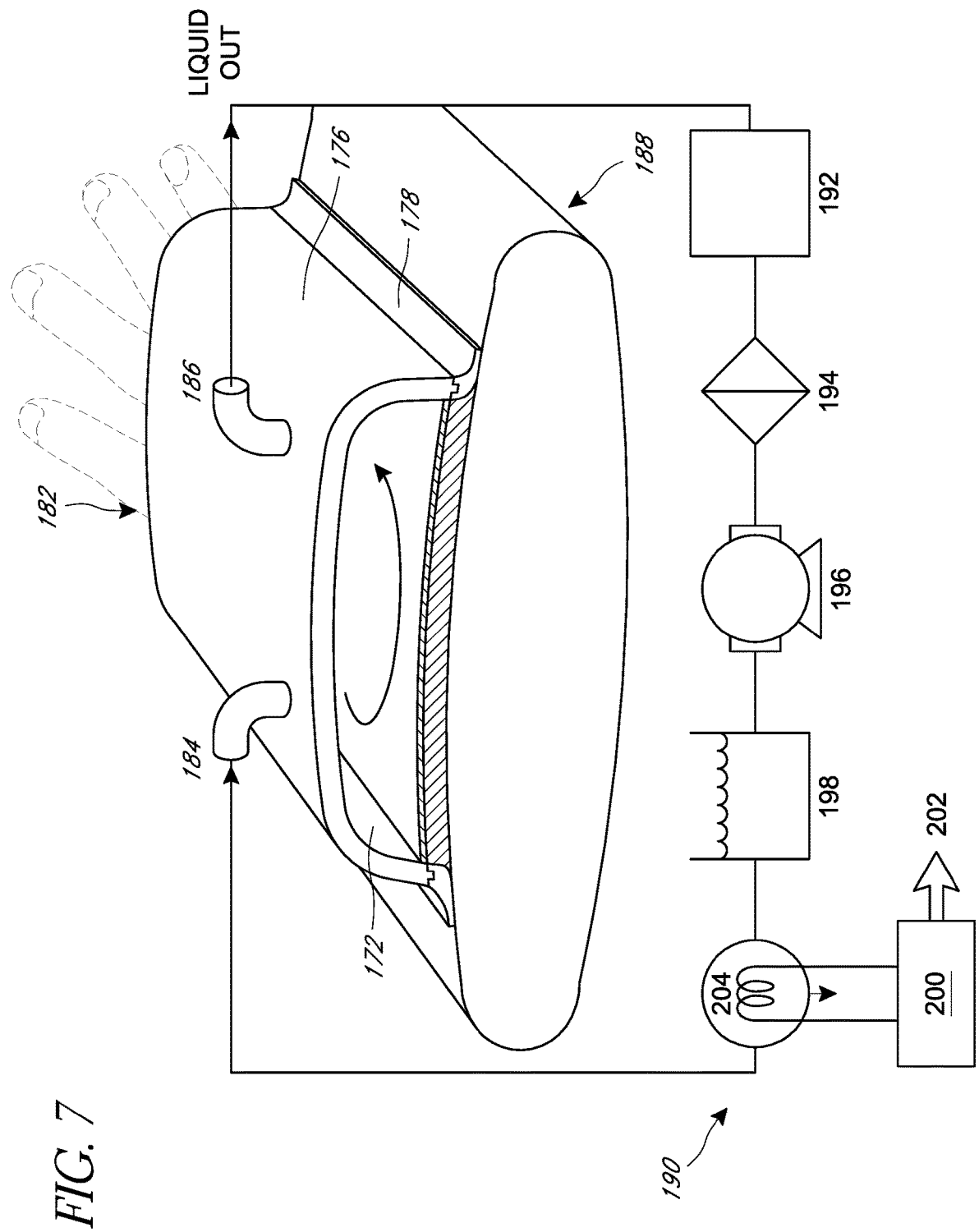
FIG. 7 illustrates a schematic of one concept for forcing a liquid coolant over the skin of a hand.

FIG. 7 illustrates a schematic of one concept for forcing a liquid coolant over the skin of a hand 188. Liquids such as water and glycol have much higher specific heats than air and therefore can carry away far more heat for the same flow. Here the cool liquid enters the end effector 182 inlet 184 and exits the end effector outlet 186 carrying heat away. The warm liquid enters the heat removal device 190 and encounters a flow, temperature and pressure sensor 192. This pressure sensor is used to ensure the chamber is maintained at negative pressure relative to ambient.

The liquid passes through appropriate filtration 194, a pump 196, and enters a reservoir 198. It may be chilled 200, e.g., via refrigeration loop 204 in the reservoir 198 or immediately thereafter. It passes through another sensor array (not shown in the image) before heading back toward the end effector 182. The cooling media may be saline, water, gel or other suitable liquid.

In some embodiments disclosed is a thermally-conductive interface. The thermally-conductive interface concept can be similar to that described in FIG. 7 above but instead of air contacting the skin, a conductive material contacts the skin. This material may be a highly conductive metal or it may be a very thin material of lower conductivity (thin film). Heat is removed from the skin through direct conductivity. Heat is removed from the conductive material via any number of ways. Example mechanisms for removal of heat from conductive materials include:

1. Convective transfer to cool air passing over backside (opposite skin) of conductive material.
2. Convective transfer to a cooling liquid passing over backside of conductive material.
3. Direct conduction into a thermo-electric cooler mounted on the backside of the conductive material.

The human body accomplishes significant cooling via radiation in the infrared band to surroundings at room temperature.

Figure 8:
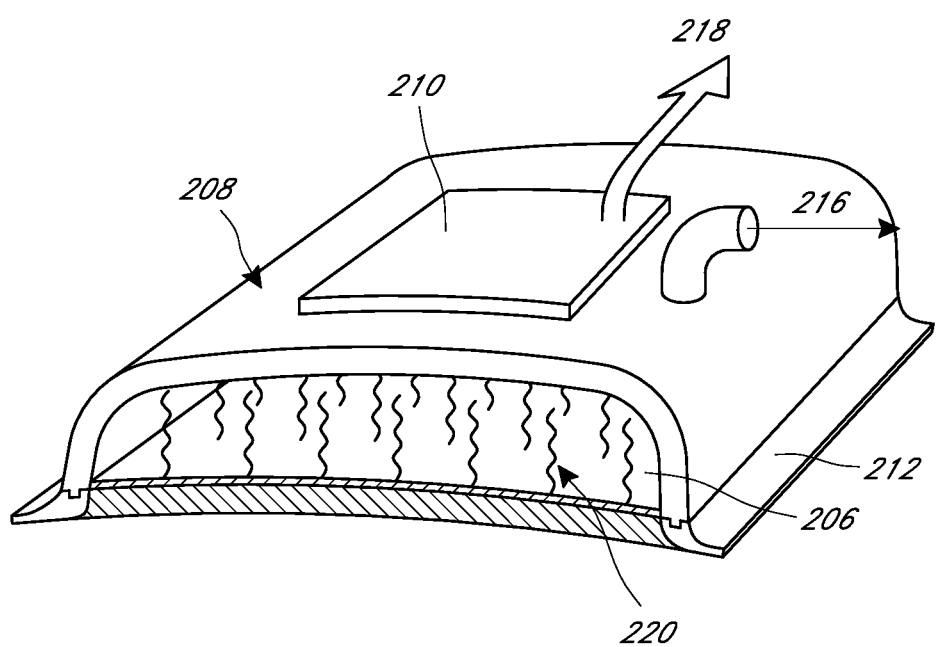
FIG. 8 illustrates an embodiment that leverages a heat loss mechanism.

FIG. 8 illustrates an embodiment that leverages this heat loss mechanism. An inner chamber 206 is established with a slightly negative pressure generated via vacuum 216 relative to ambient. In this case, there is no need for constant flow of air or liquid; therefore the vacuum generation needs are much less. The rigid housing 208 forms a cool target with high emissivity, and includes a seal region 212 that can be as previously described. The inside of the housing 208 may be painted or textured or both to increase the emissivity. The housing 208 can in some cases be thermally conductive to aid in distributing the cool temperatures. Heat 218 is extracted from all or a portion of the housing 208 by a cooling block 210. The cooling block 210 may extract this heat in a number of ways.

Non-limiting examples of mechanisms for the cooling block 210 to remove heat from the housing 208 are:

1. Convective transfer to cool air passing over ventral surface (glabrous tissue) of conductive material.
2. Convective transfer to a cooling liquid passing over ventral surface (glabrous tissue) of conductive material.
3. Direct conduction into a thermo-electric cooler mounted on ventral surface (glabrous tissue) of the conductive material.

In an alternate embodiment the chamber is not hollow but filled with an IR transmissive foam or elastomeric material (ex. Polyethylene foam). This allows the IR energy 220 to pass through but also provides some support between the skin and housing. This may allow the housing 208 to be semi-rigid rather than rigid.

At temperatures around room temperature, radiant heat transfer is a primary form of heat loss. Utilizing radiant heat loss is useful because the system's heat sink need not be in contact with the skin. Therefore, the heat sink can have a lower enthalpy than that of convective and or conductive mediums. Kirchov's Law of thermal radiation notes that heat transfers well between near field bodies when the radiant body has a high emissivity. Absorbing bodies collect radiation if they have a high absorption rate. Emissivity and absorption rates are nearly identical for most mediums. Skin has an emissivity rate of 0.97 out of 1 and is a near perfect thermal radiator.

For cooling the body, heat transfer out of the body is considered. The Stefan-Boltzmann Law states that if a hot object is radiating energy (Q/t) to its cooler surroundings at temperature $T^4_{cold}$, the net radiation loss rate takes the following form:

$$\frac{Q}{t} = e\sigma A(T^4_{hot} - T^4_{cold})$$

Figure 9:
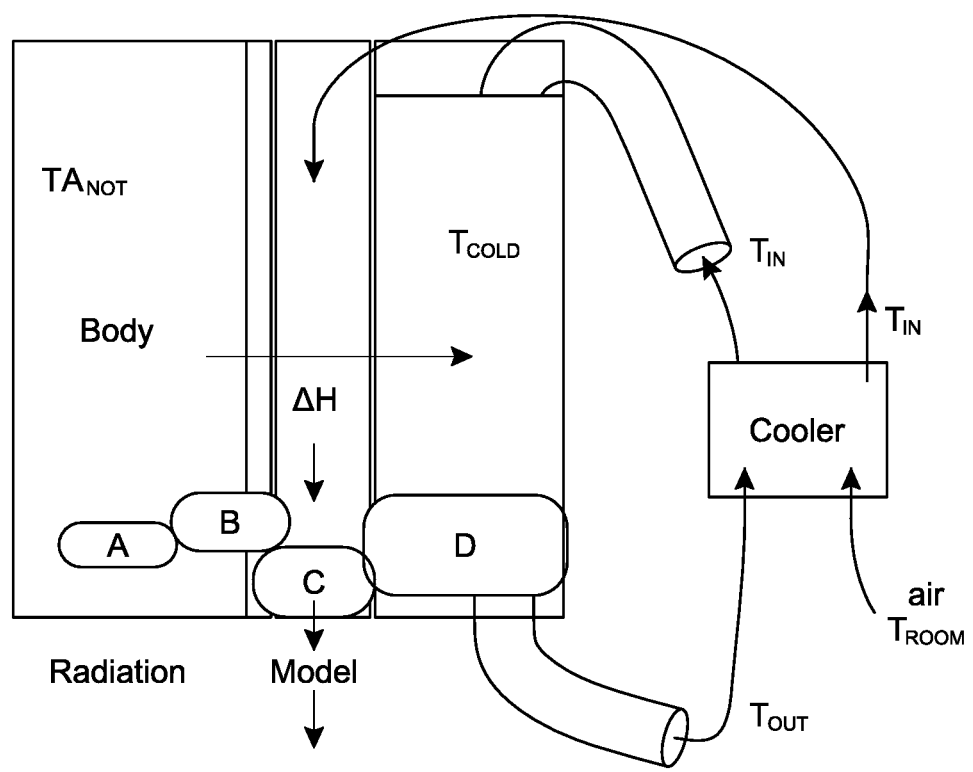
FIG. 9 schematically illustrates Radiant Thermal Zones demonstrating a modeled hybrid thermal transfer heat sink.

FIG. 9 schematically illustrates radiant thermal zones illustrating a modeled Hybrid thermal transfer heat sink to remove heat from Zone A below the epidermis, into the skin (epidermal layer) in Zone B. This is done naturally by the body if the Temperature of the skin Ta is colder than body temp, or Ta. The skin is a near perfect radiator with an emissivity of 0.97 (e=0.97). Heat is then transferred from the body via the skin in Zone B, through a medium in Zone C and absorb by a cooler medium (heat sink) in Zone D. Zone C could be air or reduced humidity air. Zone D would have a high coefficient of thermal absorption (α~1). The heat sink in Zone D could then have a heat exchanger that would pump heat out of component D and into an internal or external cooler. It is well known that coolers emit heat. Heat from the cooler then could be routed away from the body. A secondary heating loop could be monitored and regulated for temperature and pressure. This loop could be restricted and/or valved, mixed with ambient air, and fed back into zone C to help regulate skin temperature and hypothalamus sensation if a control system is used to increase skin and/or core temperature to aid with comfort and/or avoidance of arrector pili muscle engagement and/or shivering. The secondary loop can be intermittent, constant, and/or cycled. The secondary loop can include sensors and/or a fan to induce convection. Zone C could include a low absorption air barrier such that the return (warm air) does not cool Zone D. The secondary loop air circuit can include a means to dehumidify the air prior to entering Zone C. The secondary loop could be used to wick away perspiration. The secondary loop could also have a valve that can redirect all of the heat away from the body. The valve could be electronically or mechanically actuated to adjust secondary heating temperature. Vacuum could be created in Zone C by establishing vacuum on the exiting air while physically confining Zone C. Alternately, static vacuum cups with low a absorption coefficients could be used to hold vacuum. In this example the primary heat transfer mechanism will be radiant heat loss to Zone D. Heat gain and/or loss will present in the form of convection to the air in Zone C. Zone C could contain a porous or open support structure that could be either flexible or stiff, to ensure that Zone D does not touch the skin in Zone B.

Figure 10:
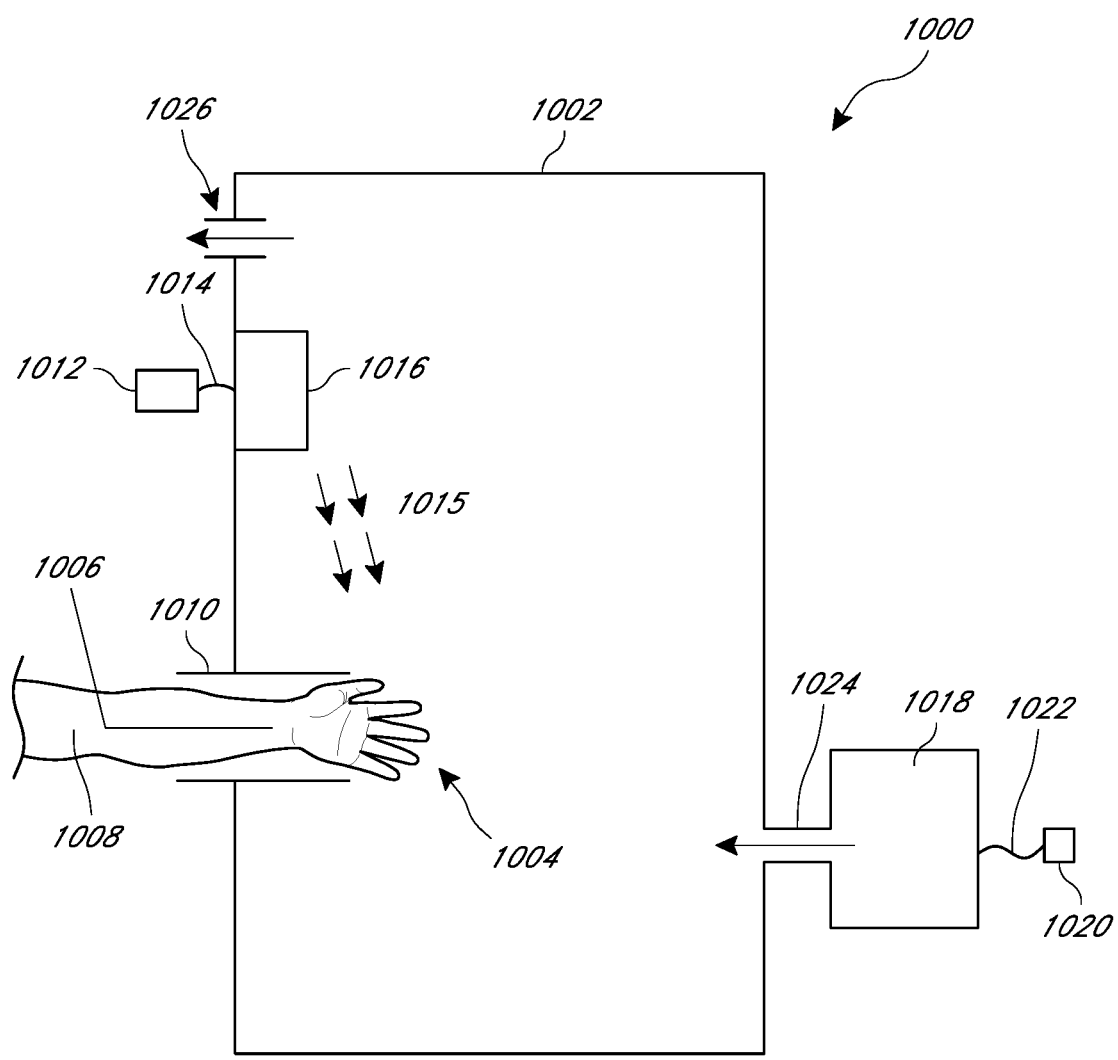
FIG. 10 illustrates a system and method for treating a patient, including a device including a chamber configured to preferentially control one or more environmental factors, such as, for example, the humidity, atmospheric pressure, and/or temperature of the air surrounding selected glabrous tissue of a patient.

FIG. 10 illustrates a system and method for treating a patient, including a device 1000 including a chamber 1002 configured to preferentially control one or more environmental factors, such as, for example, the humidity, atmospheric pressure, and/or temperature of the air surrounding selected glabrous tissue 1004 of a patient (e.g., one or more hands and/or feet of the patient), while not affecting the humidity and/or temperature of the air surrounding the rest 1108 of the patient. As illustrated, glabrous tissue, such as the hand 1004 of a patient can be inserted through port 1010 that can be made of plastic, rubber, latex, or other appropriate material. In some embodiments, the material of the port 1010 can create an air-tight or semi air-tight seal to maintain a gradient, such as a humidity and/or temperature gradient between the interior and the exterior of the chamber 1002. In some embodiment, a rubber band or other feature (not shown) can help to create the seal. Operably connected to the interior of the chamber 1016 are one, two, or more convection elements such as fan 1016 configured to direct air toward the glabrous tissue 1004 within the interior of the chamber 1002. Also operably connected the chamber 1016 is a conduit 1014 to a power supply 1012, which can be connected to a power outlet, such as AC power, a battery, or other energy source to power one or more components of the device 1000. The battery can be rechargeable which may be advantageous for portable devices 1000. Also illustrated is a factor control element such as gas compressor 1018 having an inlet 1024 into the interior of the chamber 1002. The compressor 1018 can be configured to deliver a gas, such as air, nitrogen, oxygen, helium, or a combination thereof for example with a specified humidity into the interior of the chamber. In some embodiments, the compressor can be an oxygenator such as an oxygen nebulizer that provides dehumidified or humidified oxygen into the chamber at a predetermined flow rate. In some embodiments, an oxygenator is not required and the compressor can simply alter the humidity of room air. In some embodiments, the flow rate can be about, at least about, or no more than about 2, 3, 4, 5, 6, 7, 8, 9, 10, 12, 15, 20, 25, 30, 40, 50, or more or less liters per minute. The compressor can have a separate power supply 1020 via conduit 1022 as illustrated, or utilize a common power supply 1012 with the fan 1016 and/or other components. Also illustrates is one or more outlets 1026 which can allow the passive escape of gas from the interior of the chamber 1002. The outlet 1026 can include a valve or other feature to control the escape of gas from the interior of the chamber 1002. The device 1000 can also include one or more sensors configured to measure humidity, temperature, pressure, and/or other parameters (not shown) in which adjustments to humidity, convection, and other parameters can be made in real time.

Not to be limited by theory, patients can be sensitive to humidity, irrespective of a change in temperature because the human body uses evaporative cooling, enabled by perspiration, as the primary mechanism to rid itself of waste heat. Perspiration evaporates from the skin more slowly under humid conditions than under arid conditions. Humans perceive a low rate of heat transfer from the body to be equivalent to a higher air temperature. In some embodiments, exposing selected glabrous tissue to relatively lower humidity environments can be perceived physiologically by the patient via nerves in the glabrous tissue as a relatively high rate of heat transfer/loss, and thus increase the body's metabolism through hypothalamic and other mechanisms disclosed elsewhere herein to generate heat and compensate for the increased heat loss.

Not to be limited by theory, patients can also be sensitive to convection (e.g., by the use of one or more fans) without a heating or cooling stimulus per se. Convection, such as wind, can alter the perceived temperature (either being greater or less than the actual temperature) by a patient without actually altering the actual temperature. A solid surface loses heat through evaporation, conduction, and radiation. The rate of conduction depends on the difference in temperature between the surface and its surroundings. As conduction from a warm surface heats the air around it, an insulating boundary layer of warm air forms against the surface. Moving air disrupts this boundary layer, or epiclimate, allowing for cooler air to replace the warm air against the surface. The faster the wind speed, the more readily the surface cools. The effect of wind chill is to increase the rate of heat loss and reduce any warmer objects to the ambient temperature more quickly. It cannot, however, reduce the temperature of these objects below the ambient temperature, no matter how great the wind velocity. For most biological organisms, the physiological response is to generate more heat in order to maintain a surface temperature in an acceptable range. The attempt to maintain a given surface temperature in an environment of faster heat loss results in both the perception of lower temperatures and an actual greater heat loss. In other words, the air "feels" colder than it is because of the chilling effect of the wind on the skin. Use of a convection fan, either alone or in combination with a humidity-modifying agent can be advantageous in some cases in being more comfortable than subjecting a part of the patient to a significant temperature change. The use of a convection fan as well as a dehumidifier without changing the temperature surrounding the target region of the patient can be synergistic leading to unexpected results in improving, for example, metabolic syndrome, diabetes mellitus, dyslipidemia, hypertension, atherosclerosis, and/or other conditions as disclosed herein.

In some embodiments, the convection fan generates a flow of air to the target region, e.g., glabrous tissue of a patient, that is about, less than about, or more than about 500 m$^3$/h, 400 m$^3$/h, 300 m$^3$/h, 250 m$^3$/h, 225 m$^3$/h, 200 m$^3$/h, 175 m$^3$/h, or 150 m$^3$/h. In some embodiments, the convection fan is configured to generate a wind speed to the target region that is about or at least about 5 mph, 10 mph, 15 mph, 20 mph, 25 mph, 30 mph, 35 mph, 40 mph, or more, or various ranges thereof, such as between about 5 mph and about 20 mph, in some embodiments. In some embodiments, the convection fan generates a flow of air of about 10, 20, 30, 40, 50, 60, 70, 80, 90, 100, 110, 120, 130, 140, 150, 160, 170, 180, 190, 200, 225, 250, 275, 300, 325, 350, 375, 400, 425, 450, 475, 500, or more cubic feet per minute (CFM). In some embodiments, the convection fan is configured to generate sufficient air flow to cause heat transfer from the glabrous tissue of the skin or have another effect to stimulate adiponectin production, lipolysis, or trigger BAT activation, for example. In some embodiments, the system includes a convection fan but does not include a temperature-modifying element such as a chiller or a heater. In some embodiments, the convection fan can drive the low-humidity air toward the selected region of the patient.

The humidity within the chamber 1002 can be preset and or adjustable to any desired humidity depending on the desired clinical result. In some embodiments, the relative humidity within the chamber is set relatively low, such as less than about 35%, 30%, 25%, 20%, 15%, 10%, 5%, 4%, 3%, 2%, 1%, or less. In some embodiments, the relative humidity of the chamber can be set to between about 0% and about 30%, between about 10% and about 25%, between about 15% and about 25%, or between about 10% and about 20% in some embodiments, or about 0%, 1%, 2%, 3%, 4%, 5%, 10%, 11%, 12%, 13%, 14%, 15%, 16%, 17%, 18%, 19%, 20%, 21%, 22%, 23%, 24%, or 25%. In some embodiments, the relative humidity within the chamber 1002 can be controlled as to have a positive or negative gradient with respect to the relative humidity outside of the chamber 1002 of about 5%, 10%, 15%, 20%, 25%, 30%, or more, or various ranges thereof. In some embodiments, the device can have controls to create a relative humidity gradient within the chamber 1002 with respect to the outside of the chamber 1002 while there is no temperature gradient or no substantial temperature gradient within the chamber 1002 with respect to the outside of the chamber 1002.

In some embodiments, the relative humidity within the chamber is set relatively high, such as about or more than about 50%, 55%, 60%, 65%, 70%, 75%, 80%, 85%, 90%, 95%, or more. In some embodiments, the relative humidity of the chamber can be set to between about 60% and about 100%, between about 70% and about 95%, between about 75% and about 90%, or between about 80% and about 90% in some embodiments.

In some embodiments, the device and/or chamber itself can take the form of handwear such as a glove or mitten, and/or footwear such as a shoe or boot for example.

In some embodiments, the glabrous tissue of a patient to be treated includes one or both hands, and/or one or both feet. The tissue can be exposed to the controlled environment of the chamber for about, at least about, or no more than about 5 minutes, 10 minutes, 15 minutes, 30 minutes, 45 minutes, 1 hour, 2 hours, 3 hours, 4 hours, 5 hours, 6 hours, 7 hours, or 8 hours a day. In some embodiments, the patient is treated nocturnally, such as during sleep, and/or during waking hours. The treatment can be continuous (e.g., 3 hours straight in a day), pulsed or intermittent (e.g., 1 hour straight 3 times a day), and repeat 1, 2, 3, 4, 5, or more times daily, every other day, every third day, weekly, or other interval depending on the desired clinical result.

In some embodiments, systems and methods as disclosed herein can affect, e.g., increase or decrease the metabolic rate of a patient. In some embodiments, systems and methods as disclosed herein can affect the basal metabolic rate of a patient by at least about 2%, 3%, 4%, 5%, 6%, 7%, 8%, 9%, 10%, 12%, 15%, 20%, 25%, 30%, 35%, 40%, 45%, 50%, or more. In some embodiments, systems and methods as disclosed herein can affect the basal metabolic rate of a patient by at least 10, 20, 30, 40, 50, 60, 70, 80, 90, 100, 150, 200, 250, 300, 400, 500, or more kcal per day.

In some embodiments, systems and methods as disclosed herein can prevent or treat a variety of conditions including diabetes mellitus, gestational diabetes, prediabetes, impaired glucose tolerance, obesity, dyslipidemia (including high LDL, low HDL, and hypertriglyceridemia), metabolic syndrome, hypertension, fatty liver, coronary, cerebral, or peripheral vascular disease. In some embodiments, the systems and methods as disclosed herein can prevent or treat a neurologic or psychiatric condition, such as dementia or failure to thrive for example. In some embodiments, systems and methods as disclosed herein can prevent or treat hyperthermia or hypothermia.

Figure 11A:
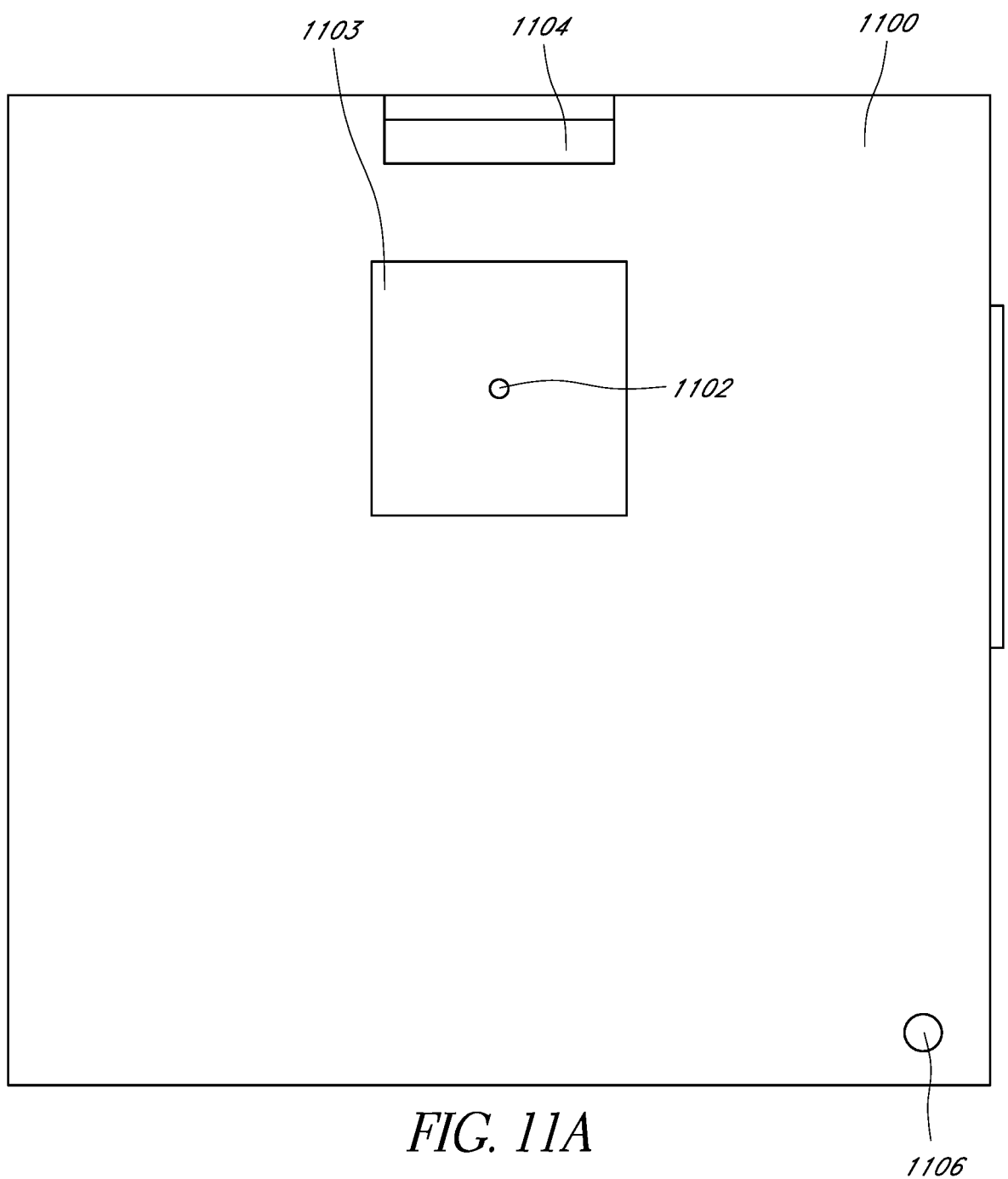
FIG. 11A illustrates a schematic side view of a humidity-controlled device having an interior chamber for treatment of metabolic syndrome or other conditions such as those disclosed herein, according to some embodiments of the invention.

FIG. 11A illustrates a schematic side view of a humidity-controlled device 1100 having an interior chamber for treatment of metabolic syndrome or other conditions such as those disclosed herein, according to some embodiments of the invention. Some features can be as described, for example, in connection with FIG. 10 above. The device 1100 in some embodiments can include a cubical or rectangular housing. In some embodiments the device can have a length of between about 6 inches and about 24 inches, such as about 12 inches; a width of between about 6 inches and about 24 inches, such as about 12 inches; a height of between about 6 inches and about 12 inches, such as about 8 inches; and a housing thickness of between about ¼ inch and about ½ inch. The device 1000 can be made of any appropriate material, and is clear acrylic in some embodiments. The device can include an adjustable exhaust outlet 1102 in which air can escape the chamber. The outlet 1102 can have a diameter of about 2 inches to about 4 inches, such as about 3 inches in some embodiments Also shown is attachment collar 1103 extending outwardly at least about ¾" in some embodiments. The device 1100 can also include a mounting area 1104 (such as about 3" by 3" in some cases) for attaching an air-circulating element, such as a fan. Air supply inlet 1106 is also shown, which can supply dehumidified air into the chamber. In some embodiments, the air supply inlet can have a diameter of between about ¼ inch and about 2 inch, such as about ⅜ inches in some embodiments).

Figure 11B:
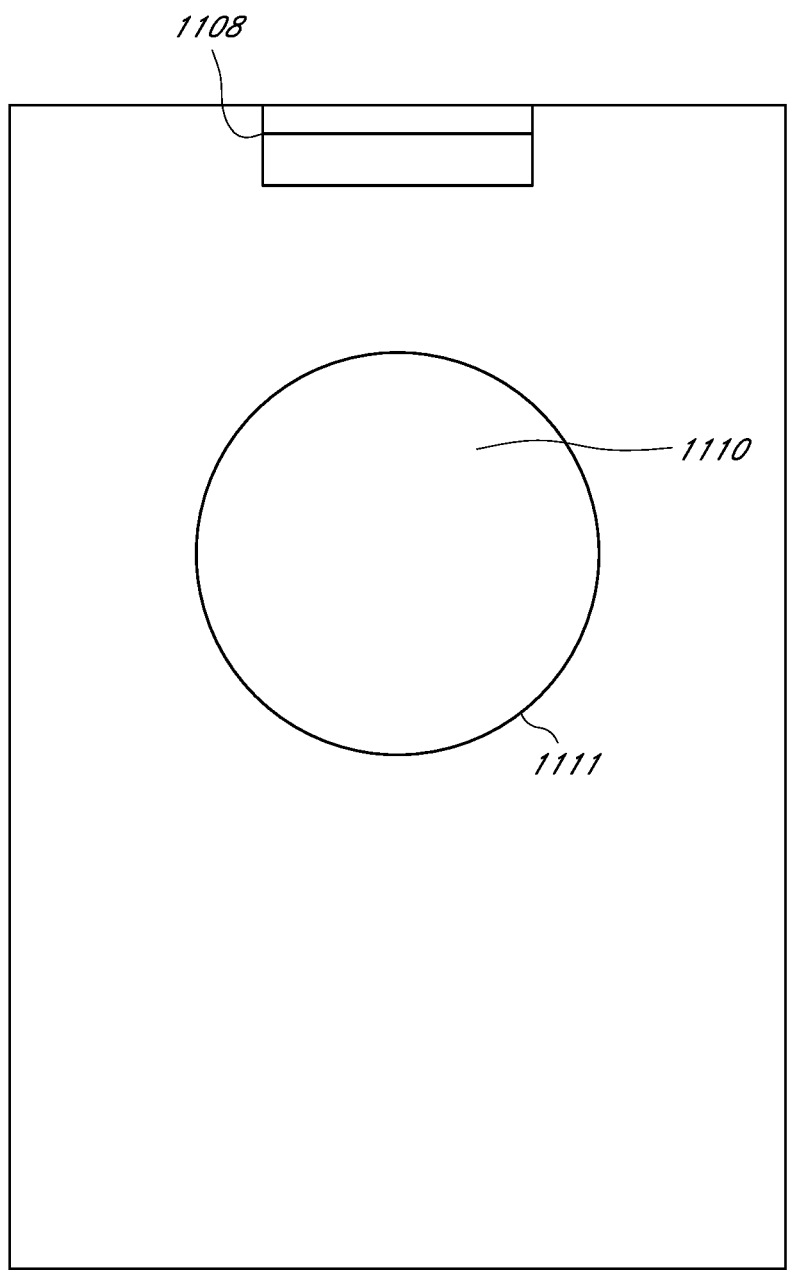
FIG. 11B is a schematic end view of the device shown in FIG. 11A.
Figure 11C:
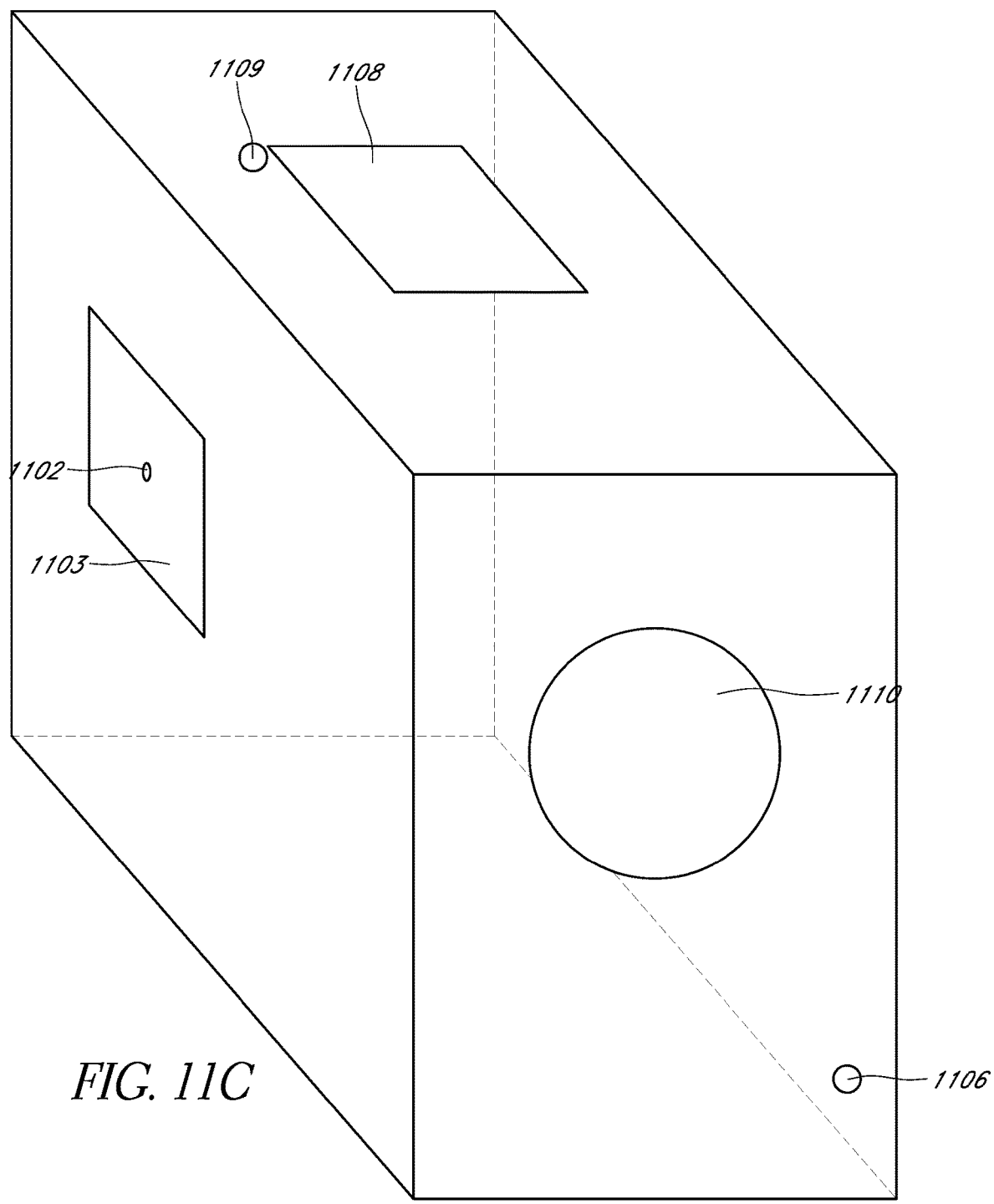
FIG. 11C is a perspective view of the device of FIGS. 11A-11B.

FIG. 11B is a schematic end view of the device 1100 shown in FIG. 11A, showing patient port 1110 for the insertion of a patient's extremity that includes glabrous tissue into the chamber 1110. Attached to the sidewall of the chamber is seal material 1111 for creating an air-tight or substantially air-tight seal as previously describe. Also shown is air-circulating element 1108. FIG. 11C is a perspective view of the device 1100 of FIGS. 11A-11B, showing fan 1108, an aperture 1109 for the power conduit of the fan 1108. Also shown are adjustable exhaust outlet 1102 and attachment collar 1103, patient port 1110, and air supply inlet 1106.

In some embodiments, systems as described herein can further include a vacuum. The vacuum is in operative communication with the chamber by way of a vacuum line. The vacuum can be used to exert negative pressure on the glabrous skin on which the device is controlling the humidity of the air surrounding the glabrous tissue, or other parameter. The negative pressure can be used to enhance the dilatation of AVAs in the subject's glabrous skin. The vacuum and therefore the negative pressure exerted on the glabrous skin can be controlled by a computer. The vacuum can be in operative communication with the computer by way of a vacuum module. In addition, the device can be equipped with a pressure sensor that is in operative communication with the computer by way of a pressure sensing module. In this way, the computer may process pressure information and humidity information and this information may be used to adjust factors affecting the operation of the device such as the humidity or temporal characteristics of the dehumidified air circulated through the device or the negative pressure or temporal characteristics thereof.

Sensors may be in operative communication with a computer through a sensor module. In addition, the compressor can also be in operative communication with the computer through a compressor module to adjust flow rate, relative humidity, etc. Information collected from the humidity sensors that may be present within the chamber can be used to adjust the relative humidity of the chamber to a desired level.

As shown in the systems disclosed herein, the methods described herein can be implemented via a general-purpose computing device in the form of a computer. The components of the computer can include, but are not limited to, one or more processors or processing units, a system memory, and a system bus that couples various system components including the processor to the system memory.

The system bus may represent one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. The bus, and all buses specified in this description, can also be implemented over a wired or wireless network connection and each of the subsystems, including the processor, a mass storage device, an operating system, application software, data, a network adapter, system memory, an Input/Output Interface, a display adapter, a display device, and a human machine interface, can be contained within one or more remote computing devices at physically separate locations, connected through buses of this form, in effect implementing a fully distributed system.

The computer typically includes a variety of computer readable media. Such media can be any available media that is accessible by the computer and includes both volatile and non-volatile media, removable and non-removable media. The system memory includes computer readable media in the form of volatile memory, such as random access memory (RAM), and/or non-volatile memory, such as read only memory (ROM). The system memory typically contains data such as data and/or program modules such as operating system and application software that are immediately accessible to and/or are presently operated on by the processing unit. The computer may also include other removable/non-removable, volatile/non-volatile computer storage media. A mass storage device can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device, including by way of example, an operating system and application software. Each of the operating system and application software (or some combination thereof) may include elements of the programming and the application software. Data can also be stored on the mass storage device. Data can be stored in any of one or more databases known in the art. Examples of such databases include, DB2, Microsoft Access, Microsoft SQL Server, Oracle mySQL, PostgreSQL, and the like. The databases can be centralized or distributed across multiple systems.

A user can enter commands and information into the computer via an input device. Examples of such input devices include, but are not limited to, a keyboard, pointing device (e.g., a "mouse"), a microphone, a joystick, a serial port, a scanner, and the like. These and other input devices can be connected to the processing unit via a human machine interface that is coupled to the system bus, but may be connected by other interface and bus structures, such as a parallel port, game port, or a universal serial bus (USB).

The computer can operate in a networked environment using logical connections to one or more remote computing devices. By way of example, a remote computing device can be a personal computer, portable computer, a server, a router, a network computer, a peer device or other common network node, and so on. Logical connections between the computer and a remote computing device can be made via a local area network (LAN) and a general wide area network (WAN). Such network connections can be through a network adapter. A network adapter can be implemented in both wired and wireless environments. Such networking environments are commonplace in offices, enterprise-wide computer networks, intranets, and the Internet.

An implementation of application software may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Example 1

A 62 year-old male patient with metabolic syndrome, coronary artery disease status-post stenting, dyslipidemia, obesity, and diabetes mellitus was treated daily for approximately 3 hours over a 2 week period by placing a hand in a dehumidified sealed chamber (relative humidity 16%) without controlling the temperature of the chamber, which remained at room temperature. Relative humidity outside of the chamber was about 40%. The patient did not change his lifestyle habits, medication regimen, or diet over the 2 week period. The patient's lab comparison showed surprising improvements in HbA1c, LP-IR score, fasting serum glucose, total cholesterol, and LDL-C. The patient tolerated the procedures without complications.

| Lab test | Pre-Treatment | 2 weeks thereafter | Units |
|---|---|---|---|
| HbA1c | 7.9 | 7.7 | % |
| Insulin | 38.8 | 20.2 | Uiu/mL |
| LP-IR Score | 68 | 57 | |
| Fasting Serum glucose | 141 | 108 | mg/dL |
| Total cholesterol | 165 | 146 | mg/dL |
| HDL-C | 38 | 37 | mg/dL |
| LDL-C | 99 | 87 | mg/dL |
| Triglycerides | 138 | 110 | mg/dL |
| Leptin | 16.6 | 15.1 | ng/mL |

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning glabrous tissue of a patient's extremity in a humidity-controlled chamber" include "instructing the positioning glabrous tissue of a patient's extremity in a humidity-controlled chamber." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system for modulating glabrous tissue of a patient, comprising:
   a chamber configured to receive a portion of the patient comprising the glabrous tissue;
   a compressor configured to supply a gas to an interior of the chamber sufficient to transfer heat away from the glabrous tissue, the gas having a relative humidity of less than about 35%;
   a patient port operably connected to the chamber, the patient port configured to allow insertion of the portion of the patient into the chamber and a seal to be formed;
   a fan configured to direct gas to the glabrous tissue; and
   a controller configured to adjust the relative humidity of the gas,
   wherein the system is not configured to alter a temperature or pressure of the interior of the chamber.

2. The system of claim 1, further comprising a vacuum.

3. The system of claim 1, further comprising a sensor.

4. The system of claim 1, wherein the housing comprises a length between 6 inches and 24 inches.

5. The system of claim 1, wherein the compressor is configured to deliver air, nitrogen, oxygen, helium, or a combination of gases.

6. The system of claim 1, wherein the controller is further configured to control the rate of flow.

7. The system of claim 1, wherein the controller is configured to adjust the relative humidity based on an input from one or more sensors.

8. A method for treating a patient, comprising:
   inserting a portion of the patient comprising glabrous tissue into a patient port operably connected to a chamber, the patient port forming a seal;
   supplying a gas to an interior of the chamber sufficient to transfer heat away from the glabrous tissue, the gas having a relative humidity of less than about 35%; and
   directing gas to the glabrous tissue by a fan,
   wherein the method does not alter a temperature or pressure of the interior of the chamber.

9. The method of claim 8, wherein air surrounding the patient outside of the chamber has a higher relative humidity.

10. The method of claim 8, further comprising adjusting the relative humidity of the gas.

11. The method of claim 8, wherein the method increases metabolism.

12. The method of claim 8, wherein the method promotes overall weight loss by enhanced caloric loss.

13. The method of claim 8, wherein the method improves insulin resistance.

14. The method of claim 8, wherein the method stimulates adiponectin production.

15. The method of claim 8, wherein the method increases glucose uptake.

16. The method of claim 8, wherein the method normalizes lipid metabolism.

17. The method of claim 8, wherein the method reduces vascular smooth muscle proliferation.

18. The method of claim 8, wherein the method causes vasodilation and blood pressure reduction.

19. The method of claim 8, wherein the method triggers lipolysis.

20. The method of claim 8, wherein the method activates brown adipose tissue.

\* \* \* \* \*